(12) United States Patent
Forgez

(10) Patent No.: US 10,077,303 B2
(45) Date of Patent: Sep. 18, 2018

(54) ANTI-NEUROTENSIN ANTIBODIES AND USES THEREOF

(71) Applicants: INSERM (INSTITUT NATIONAL DE LA SANTÉ ET DE LA RECHERCHE MÉDICALE), Paris (FR); UNIVERSITÉ PARIS DESCARTES, Paris (FR)

(72) Inventor: Patricia Forgez, Paris (FR)

(73) Assignees: INSERM (Institut National de la Sante et de la Recherche Medicale), Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 15/314,975

(22) PCT Filed: Jun. 1, 2015

(86) PCT No.: PCT/EP2015/062168
§ 371 (c)(1),
(2) Date: Nov. 30, 2016

(87) PCT Pub. No.: WO2015/185513
PCT Pub. Date: Dec. 10, 2015

(65) Prior Publication Data
US 2017/0233470 A1 Aug. 17, 2017

(30) Foreign Application Priority Data

Jun. 2, 2014 (EP) ..................................... 14305825

(51) Int. Cl.
| A61K 39/00 | (2006.01) |
| C07K 16/26 | (2006.01) |
| A61K 39/395 | (2006.01) |
| A61K 33/24 | (2006.01) |
| A61K 45/06 | (2006.01) |

(52) U.S. Cl.
CPC .............. *C07K 16/26* (2013.01); *A61K 33/24* (2013.01); *A61K 39/3955* (2013.01); *A61K 45/06* (2013.01); *A61K 39/39558* (2013.01); *A61K 2039/505* (2013.01); *C07K 2317/24* (2013.01); *C07K 2317/56* (2013.01); *C07K 2317/565* (2013.01); *C07K 2317/73* (2013.01); *C07K 2317/76* (2013.01)

(58) Field of Classification Search
CPC ..................... A61K 39/39558; A61K 2039/505
See application file for complete search history.

(56) References Cited

FOREIGN PATENT DOCUMENTS

WO 2010/069929 A1 6/2010

OTHER PUBLICATIONS

Cho et al. (Cancer Res. Nov. 15, 2013; 73 (22): 6770-9; pp. 1-17).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Winkler et al. (J. Immunol. Oct. 15, 2000; 165 (8): 4505-4514).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Wang et al. (Leuk. Lymphoma. Sep. 2002; 43 (9): 1827-1835).*
Rosenwald et al. (Leuk. Lymphoma. 2003; 44 (Suppl. 3): S41-S47).*
Mihal et al. (Neoplasma. 1997; 44 (2): 133-136).*
Luciano et al. (Leukemia. Apr. 2002; 16 (4): 700-707).*
Hara et al. (Cancer Sci. Jul. 2008; 99 (7): 1471-8).*
Saijo et al. (Cancer Sci. Oct. 2004; 95 (10): 772-776).*
Mannweiler et al. (Pathol. Oncol. Res. 2009; 15: 167-172).*
Lewis et al. (Cancer Immunology and Immunotherapy. 1993; 37: 255-263).*
Kelland (Eur. J. Cancer. Apr. 2004; 40 (6): 827-836).*
Schuh (Toxicologic Pathology. 2004; 32 (Suppl. 1): 53-66).*
Dennis (Nature. Aug. 7, 2006; 442: 739-741).*
Bibby (Eur. J. Cancer. Apr. 2004; 40 (6): 852-857).*
Peterson et al. (Eur. J. Cancer. 2004; 40: 837-844).*
Suggitt et al. (Clin. Cancer Res. Feb. 1, 2005; 11: 971-981).*
Sawyer et al. (Oncogene. Aug. 20, 1998; 17 (7): 919-24).*

(Continued)

*Primary Examiner* — Stephen L Rawlings
(74) *Attorney, Agent, or Firm* — W&C IP

(57) ABSTRACT

The present invention relates to a neutralizing antibody which is capable of binding to neurotensin with high affinity. The antibody of the present invention neutralizes the activity of neurotensin, in particular the oncogenic activities of neurotensin. In particular, the present invention relates to a neutralizing antibody which binds to the human neurotensin long fragment, and having a heavy chain variable region which comprises a H-CDR1 region having at least 90% of identity with SEQ ID NO:2 in the, a H-CDR2 region having at least 90% of identify with SEQ ID NO:3 and a H-CDR3 region having at least 90% of identity with SEQ ID NO:4; and a light chain variable region comprising a L-CDR1 region having at least 90% of identity with SEQ ID NO:6, a L-CDR2 having at least 90% of identity with SEQ ID NO:7 and a L-CDR3 region having at least 90% of identity with SEQ ID NO:8. The present invention also provides the use of such antibodies in the treatment of cancer.

10 Claims, 9 Drawing Sheets

Figure 1:
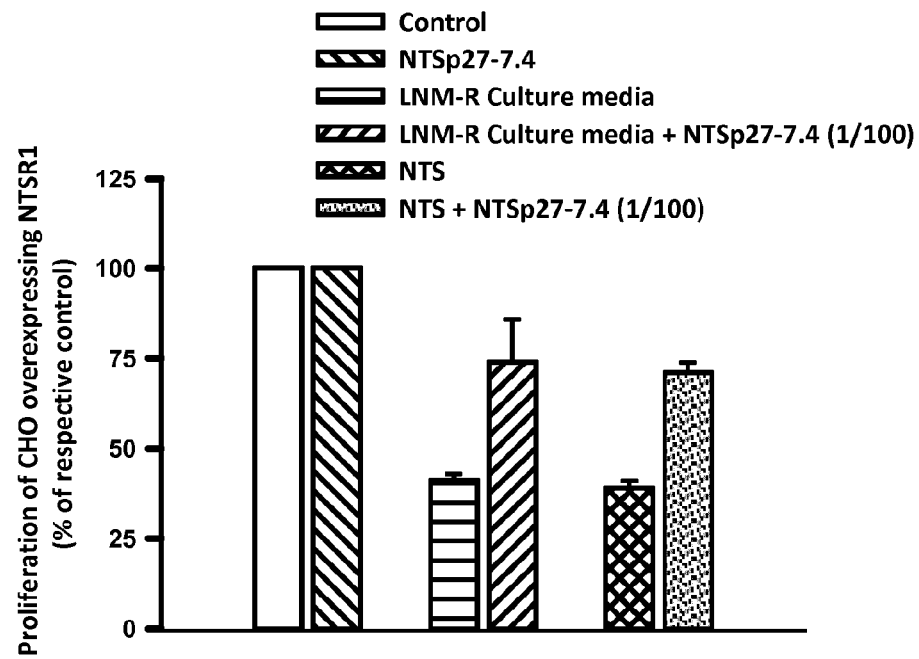

Specification includes a Sequence Listing.

(56) References Cited

OTHER PUBLICATIONS

Winler et al., "Changing the antigen binding specificity by single point mutations of an anti-p24 (HIV-1) antibody", The Journal of Immunology, Oct. 15, 2000, pp. 4505-4514, vol. 165, No. 8, The American Association of Immunologists, US.

McKay et al., "Tolerance to single, but not multiple, amino acid replacements in antibody V-H CDR2: A means of minimizing B cell wastage from somatic hypermutation?", The Journal of Immunology, Jan. 1, 1996, pp. 3285-3291, vol. 156, No. 9, The American Association of Immunologists, US.

Maynard et al., "Protection against anthrax toxin by recombinant antibody fragments correlates with antigen affinity", Nature Biotechnology, Jun. 1, 2002, pp. 597-601, vol. 20, No. 6, Nature Publishing Group, NY.

Barderas et al., "Affinity maturation of antibodies assisted by in silico modeling", Proceedings of the National Academy of Sciences, Jul. 1, 2008, pp. 9029-9034, vol. 105, No. 26, National Academy of Sciences, US.

Raiees et al., "Cross-neutralizing activity of human anti-V3 monoclonal antibodies derived from non-B clade HIV-1 infected individuals", Virology, May 1, 2013, pp. 81-88, vol. 439, No. 2.

Carray et al., "Involvement of neurotensin in cancer growth: Evidence, mechanisms and development of diagnostic tools", Peptides, Oct. 1, 2006, pp. 2445-2460, vol. 27, No. 10, Elsevier, Amsterdam, NL.

* cited by examiner

SEQUENCE LISTING

<160> NUMBER OF SEQ ID NOS: 10

<210> SEQ ID NO 1
<211> LENGTH: 122
<212> TYPE: PRT
<213> ORGANISM: Artificial
<220> FEATURE:
<223> OTHER INFORMATION: Synthetic VH sequence

<400> SEQUENCE: 1

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Gly Tyr
            20                  25                  30

Tyr Met Ser Trp Val Arg Gln Thr Pro Glu Lys Arg Leu Glu Leu Val
        35                  40                  45

Ala Ala Ile Asn Asn Tyr Gly Asp Asn Thr Asn Tyr Pro Asp Thr Val
    50                  55                  60

Lys Gly Arg Phe Ser Val Ser Arg Asp Asn Ala Lys Asn Thr Leu Tyr
65                  70                  75                  80

Leu Glu Met Asn Ser Leu Lys Ser Glu Asp Thr Ala Leu Tyr Tyr Cys
                85                  90                  95

Ala Arg Leu Ala Asn Tyr Ala Asn Gln Arg Gly Ala Met Asp Tyr Trp
            100                 105                 110

Gly Gln Gly Thr Ser Val Thr Val Ser Ser
        115                 120

<210> SEQ ID NO 2
<211> LENGTH: 10
<212> TYPE: PRT
<213> ORGANISM: Artificial
<220> FEATURE:
<223> OTHER INFORMATION: Synthetic H-CDR1

<400> SEQUENCE: 2

Gly Phe Thr Phe Ser Gly Tyr Tyr Met Ser
1               5                   10

<210> SEQ ID NO 3
<211> LENGTH: 17
<212> TYPE: PRT
<213> ORGANISM: Artificial
<220> FEATURE:
<223> OTHER INFORMATION: Synthetic H-CDR2

<400> SEQUENCE: 3

Ala Ile Asn Asn Tyr Gly Asp Asn Thr Asn Tyr Pro Asp Thr Val Lys
1               5                   10                  15

Gly

<210> SEQ ID NO 4
<211> LENGTH: 13
<212> TYPE: PRT
<213> ORGANISM: Artificial
<220> FEATURE:
<223> OTHER INFORMATION: Synthetic H-CDR3

<400> SEQUENCE: 4

Leu Ala Asn Tyr Ala Asn Gln Arg Gly Ala Met Asp Tyr
1               5                   10

<210> SEQ ID NO 5

```
<211> LENGTH: 107
<212> TYPE: PRT
<213> ORGANISM: Artificial
<220> FEATURE:
<223> OTHER INFORMATION: Synthetic VL sequence

<400> SEQUENCE: 5

Asp Ile Gln Met Thr His Thr Thr Ser Ser Leu Ser Ala Ser Leu Gly
1               5                   10                  15

Asp Arg Val Thr Ile Ser Cys Arg Ala Ser Gln Asp Ile Ala Asn Tyr
            20                  25                  30

Leu Asn Trp Tyr Gln Gln Lys Pro Asp Gly Thr Val Thr Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Asp Gln
65                  70                  75                  80

Glu Asp Ile Ala Thr Tyr Phe Cys Gln Gln Gly Tyr Thr Leu Pro Pro
                85                  90                  95

Thr Phe Gly Gly Gly Thr Lys Leu Glu Ile Lys
            100                 105

<210> SEQ ID NO 6
<211> LENGTH: 11
<212> TYPE: PRT
<213> ORGANISM: Artificial
<220> FEATURE:
<223> OTHER INFORMATION: Synthetic L-CDR1

<400> SEQUENCE: 6

Arg Ala Ser Gln Asp Ile Ala Asn Tyr Leu Asn
1               5                   10

<210> SEQ ID NO 7
<211> LENGTH: 7
<212> TYPE: PRT
<213> ORGANISM: Artificial
<220> FEATURE:
<223> OTHER INFORMATION: Synthetic L-CDR2

<400> SEQUENCE: 7

Tyr Thr Ser Arg Leu His Ser
1               5

<210> SEQ ID NO 8
<211> LENGTH: 9
<212> TYPE: PRT
<213> ORGANISM: Artificial
<220> FEATURE:
<223> OTHER INFORMATION: Synthetic L-CDR3

<400> SEQUENCE: 8

Gln Gln Gly Tyr Thr Leu Pro Pro Thr
1               5

<210> SEQ ID NO 9
<211> LENGTH: 170
<212> TYPE: PRT
<213> ORGANISM: Homo sapiens

<400> SEQUENCE: 9

Met Met Ala Gly Met Lys Ile Gln Leu Val Cys Met Leu Leu Leu Ala
1               5                   10                  15
```

```
Phe Ser Ser Trp Ser Leu Cys Ser Asp Ser Glu Glu Glu Met Lys Ala
                20                  25                  30

Leu Glu Ala Asp Phe Leu Thr Asn Met His Thr Ser Lys Ile Ser Lys
            35              40                  45

Ala His Val Pro Ser Trp Lys Met Thr Leu Leu Asn Val Cys Ser Leu
        50              55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
                100                 105                 110

Ser Arg Ala Phe Gln His Trp Glu Leu Ile Gln Glu Asp Ile Leu Asp
            115                 120                 125

Thr Gly Asn Asp Lys Asn Gly Lys Glu Glu Val Ile Lys Arg Lys Ile
        130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 10
<211> LENGTH: 14
<212> TYPE: PRT
<213> ORGANISM: Artificial
<220> FEATURE:
<223> OTHER INFORMATION: Synthetic antigen peptide

<400> SEQUENCE: 10

Cys Gln Leu Tyr Glu Asn Lys Pro Arg Arg Pro Tyr Ile Leu
1               5                   10
```

ANTI-NEUROTENSIN ANTIBODIES AND USES THEREOF

FIELD OF THE INVENTION

The present invention relates to anti-neurotensin antibodies and uses thereof.

BACKGROUND OF THE INVENTION

Neurotensin (NTS) is a 13 amino-acid peptide, discovered by Carraway and Leeman in 1973 (1). Its action as a neuromodulator in the central nervous system has been extensively studied since its discovery and continues to be the focus of many studies. In the periphery, NTS is released from the entero-endocrine N cells of the gastrointestinal tract in response to intraluminal lipid ingestion (2). The peptide predominantly exerts hormonal and neurocrine regulation on the digestive process including the inhibition of small bowel motility and gastric acid secretions, the stimulation of pancreatic and biliary secretions, and the facilitation of fatty acid absorption (3). NTS action is mediated by two different G protein coupled receptors, the high and low affinity neurotensin receptors NTSR1 and NTSR2, respectively, and by a non-specific single transmembranous sorting receptor encoded by the SORT1 gene, NTSR3/sortiline (4).

In addition to these physiological actions, the overall data from the literature argues in favor of a strategic role of NTS in carcinogenesis (for review see (5-7)). NTS oncogenic action has been described in numerous types of cancer cells and tumors with effects in each step of cancer progression from tumor growth, with proliferative and survival effects, to metastatic spread, with anchorage independent growth, and pro-migratory and pro-invasive effects. All these cellular events are presumably activated due to the abnormal expression of the high affinity neurotensin receptor 1 (NTSR1) during the early stages of cell transformation in relation with the Wnt/β-catenin pathway deregulation. Recent clinical data have been essential to identify the NTSR1 expression as an independent pejorative prognosis marker in breast, lung, and head and neck squamous cell carcinomas (HNSCC) (8-10).

In particular, NTS was shown to stimulate the growth of normal tissues like small bowel mucosa, colon, pancreas, stomach and adrenal cortex, and proposed in benign tumors, such as uterine leiomyomas or colon adenomas. This trophic effect was extended to cancer cells from various origins, as exogenous NTS was found to induce the growth stimulation of pancreas, colon, prostate, and small cell lung cancer cells in culture. Tritiated thymidin incorporation experiments performed on prostatic, pancreatic, and breast cancer cells showed a growth stimulatory effect resulting in the partial enhancement of DNA synthesis (11-13). Alterations to apoptosis regulation are another mechanism liable to influence tumor growth. NTS-induced anti-apoptotic effects were first described in the MCF-7 breast adenocarcinoma cell line (14). The contribution of the NTS/NTSR1 complex in tumor growth stimulation has been reported in several studies. A decrease of at least 50% in tumor volume and weight was observed in xenografts of colon and small cell lung cancer cells when animals were treated daily with a NTSR1 antagonist. This result has been since confirmed using interfering RNA. In addition, these experiments revealed an additional effect on tumor growth as NTSR1 expression was completely abolished in breast and non-small cell lung carcinomas (NSCLC) experimental tumors (8, 15). In accordance with these findings, exogenous NTS was also shown to significantly increase the size, weight, and DNA synthesis of MC26 colon cancer cells, and MIA Paca-2 pancreatic cancer cells xenografted in nude mice (16, 17). In the same vein, sustained administration of NTS promoted experimental-induced carcinogenesis, such as N-nitrosomorpholine induced hepatocarcinogenesis, azoxymethane-induced colon carcinogenesis, or N-methyl-N'-nitro-N-nitrosoguanidine induced gastric carcinogenesis in rats by enhancing the number and size of the neoplastic lesions as compared to the use of carcinogen alone (18, 19).

Cell migration and invasion processes are in fact prerequisites to metastatic spreading. In tumoral cells, NTS was recently shown to modulate the migratory ability of initially adherent cells, like those of glioblastoma, colon cancer, pancreatic ductal adenocarcinoma, HNSCC, and breast cancer. NTS was also shown to induce the acquisition of an invasive cellular phenotype in 3D mobility assays (20). When prostate adenocarcinoma cells, LNCaP, were submitted to NTS, a 75% increase of their basal invasive capacity was observed in MATRIGEL® (a gelatinous protein mixture). Under androgen deprivation, these prostate cancer cells became spontaneously invasive. These acquired invasive properties were correlated with intrinsically secreted NTS since the effect was abolished in the presence of specific NTS silencing (Sh-RNA). NTS agonist increased by three to four folds the number of invasive cells in MATRIGEL® (a gelatinous protein mixture) in HNSCC cells expressing NTSR1 (10).

Three major pathways induced from the activation NSTR1 by NTS have been identified. PKC is the central effector, and principal pathway by which results in ERK1/2 activation and for which subsequent proliferative and survival cellular effects are induced. The second pathway is formed from the cascade of PLC, IP3, and [Ca2+]i mobilization which regulates gene expression. The third pathway causes the activation of the small G-proteins which exert functions on cellular mobility (21).

The final oncogenic effects induced by NTS are mostly PKC-dependent. Activation of PKC by NTS was demonstrated by the use of broad isotype inhibitors, with Gö6976 the most often used as it has the advantage of preferentially inhibiting the conventional PKCs α, β, and γ (22). The use of the specific NTSR1 antagonist, SR48692, confirmed that NTSR1 mediated the effects (23). The induction of PKC activity by NTS led to the rapid activation of MAPK pathway and preferentially ERK1/2. Several pathways for MAPK cascade stimulation occurred, involving either the epidermal growth factor receptor or the direct stimulation of Raf-1, which is independent of Ras activation as it was described in K-Ras mutated human pancreatic ductal adenocarcinoma PANC-1 cells. Interestingly, in the same cell line, NTS was also shown to induce early and transient protein kinase D1 (PKD1) activity in a PKC-dependent pathway. The induction of the MAPK cascade was also further associated with the downstream induction of the early growth response gene-1 (Egr-1), and the AP-1 transcription factor c-Fos at the transcriptional and translational levels. Both mechanisms were prevented in the presence of NTSR1 antagonist. In a tumoral context, the NTS-mediated activation of the MAPK pathway is mostly associated with uncontrolled cell growth, and may exacerbate the trophic rate in various tumors.

Within the main NTS transduction pathway, PKC activation stimulates lateral pathways involving Epidermal Growth Factor Receptors transactivation in certain cancer cell lines. In the PC3 prostatic cancer cell model, NTS induced the phosphorylation of EGFR, as well as ERK1/2 and the Akt protein. This EGFR stimulation directly stems from the NTS-induced release of EGF-like ligands (HB-EGF or amphiregulin) through a PLC/PKC-dependent pathway (24, 25). The subsequent downstream signaling events led to the stimulation of the classical Ras-Raf-MEK-ERK cascade through a PI3K-dependent mechanism. In parallel, a synergistic stimulation of NTS combined to EGF was shown on DNA synthesis resulting from a prolongation of the ERK signal duration (26). Sustained NTS stimulation in lung and breast cancer cells, due to autocrine or paracrine regulation, resulted in the increase of EGFR, HER2 and HER3 expression (Dupouy et al Oncotarget 2014, Younes et al Oncotarget 2014). In parallel, the activation of metalloproteases, accompanied with the subsequent release of EFG like ligands occurred. In lung cancer cells, the metalloproteases MMP1, HB-EGF, and Neuregulin 1 were activated. In breast cancer cells MMP2, HB-EGF, and Neuregulin 2 were activated. Thus, in both model EGFR and HER3 were activated concomitantly.

NTS can modulate the activity of the small RhoGTPases Rac1, RhoA and Cdc42, which are in part responsible for the cytoskeleton dynamics known to contribute to the formation of various cytoplasmic extensions like lamellipodia, filopodia, pseudopodia, or invadopodia (27, 28).

NTS was also shown to stimulate the activity of various non-receptor tyrosine kinases by a dose-dependent phosphorylation of tyrosine residues in NSCLC. The main identified substrate corresponded to the Focal Adhesion Kinase (FAK), a protein contributing to the regulation of protein dynamics at the cell-matrix interface, and also involved in adhesion and cell migration phenomena (29). The tyrosine phosphorylation of FAK is transient and rapid, and is prevented by treatment with SR48692. The NTS/NTSR1 pathway also activated other intracellular tyrosine kinases, among them Src and Etk/Bmx, in a prostatic cancer cell line. Etk/Bmx is activated by FAK, possibly through Src, and the three activated tyrosine kinases form a signaling complex (30). This complex is potentially involved in the alternative, NTS-induced, trophic effects consecutive to androgen deprivation.

Accordingly, anti-neurotensin antibodies having neutralizing activities are highly desirable for the treatment of cancer.

SUMMARY OF THE INVENTION

The present invention relates to a neutralising antibody which is capable of binding to neurotensin with high affinity. The antibody of the present invention neutralises the activity of neurotensin, in particular the oncogenic activities of neurotensin. In particular, the present invention relates to a neutralising antibody which binds to the human neurotensin long fragment, and having a heavy chain variable region which comprises a H-CDR1 region having at least 90% of identity with SEQ ID NO:2, a H-CDR2 region having at least 90% of identify with SEQ ID NO:3 and a H-CDR3 region having at least 90% of identity with SEQ ID NO:4; and a light chain variable region comprising a L-CDR1 region having at least 90% of identity with SEQ ID NO:6, a L-CDR2 having at least 90% of identity with SEQ ID NO:7 and a L-CDR3 region having at least 90% of identity with SEQ ID NO:8. The present invention also provides the use of such antibodies in the treatment of cancer.

DETAILED DESCRIPTION OF THE INVENTION

In order to inhibit neurotensin (NTS) oncogenic properties, the inventors produced a NTS monoclonal antibody directed against NTS (i.e. NTSp27.7.4). The inventors have cloned and characterized the variable domain of the light and heavy chains of said antibody, and thus determined the complementary determining regions (CDRs) domain of said antibody as described in Table A (see EXAMPLES). The inventors demonstrate that said NTS neutralizing monoclonal antibody represents a potential drug for limiting cancer progression, and restore chemotherapy responses.

Accordingly, the present invention relates to a neutralising antibody which is capable of binding to neurotensin with high affinity. The antibody of the present invention neutralises the activity of neurotensin, in particular the oncogenic activities of neurotensin as described in the EXAMPLES. The antibodies of the present invention therefore have the advantageous property that they can inhibit the biological activity of neurotensin. Accordingly, the present invention also provides the use of such antibodies in the treatment of cancer.

In some embodiments, the present invention relates to a neutralising antibody which binds human neurotensin having a heavy chain variable region which comprises a H-CDR1 region having at least 90% of identity with SEQ ID NO:2 in the, a H-CDR2 region having at least 90% of identify with SEQ ID NO:3 and a H-CDR3 region having at least 90% of identity with SEQ ID NO:4; and a light chain variable region comprising a L-CDR1 region having at least 90% of identity with SEQ ID NO:6, a L-CDR2 having at least 90% of identity with SEQ ID NO:7 and a L-CDR3 region having at least 90% of identity with SEQ ID NO:8.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification except where otherwise indicated. The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system.

According to the invention, the antibody is isolated. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term 'neutralising antibody' describes an antibody that is capable of neutralising the biological signalling activity of neurotensin for example by blocking binding of neurotensin to its corresponding receptor. It will be appreciated that the term 'neutralising' as used herein refers to a reduction in biological signalling activity which may be partial or complete. In particular a neutralizing antibody according to the invention refers to an antibody which inhibits (partially or completely) the oncogenic properties of neurotensin. For example, said neutralizing activities are typically evaluated according to any assay des described in the EXAMPLES.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below. The ALIGN-2 sequence comparison computer program was authored by Genentech, Inc. and the source code shown in Table A below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIG. 8 below. The ALIGN-2 program should be compiled for use on a UNIX operating system, preferably digital UNIX V4.0D. All sequence comparison parameters are set by the ALIGN-2 program and do not vary.

In some embodiments, the antibody of the present invention comprises a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3.

In some embodiments, the antibody of the present invention comprises a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

In some embodiments, the antibody of the present invention comprises a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3 and a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

In some embodiments, the antibody of the present invention comprises a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

In some embodiments, the antibody of the present invention comprises a heavy chain variable region having at least 70% of identity with SEQ ID NO:1 and/or a light chain variable region having at least 70% of identity with SEQ ID NO:5.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the antibody of the present invention comprises a heavy chain variable region of having the amino acid sequence set forth as SEQ ID NO:1 and/or a light chain variable region having the amino acid sequence set forth as SEQ ID NO:5.

In some embodiments, the antibody of the present invention is a chimeric antibody, typically a chimeric mouse/human antibody. In some embodiments, the mouse/human chimeric antibody comprises the variable domains of antibody NTSp27-7.4 as defined above.

The term "chimeric antibody" refers to an antibody which comprises a VH domain and a VL domain of an antibody derived the NTSp27-7.4 antibody, and a CH domain and a CL domain of a human antibody.

In some embodiments, the antibody of the present invention is a humanized antibody. In particular, in said humanized antibody, the variable domain comprises human acceptor frameworks regions, and optionally human constant domain where present, and non-human donor CDRs, such as mouse CDRs as defined above.

According to the invention, the term "humanized antibody" refers to an antibody having variable region framework and constant regions from a human antibody but retains the CDRs of the NTSp27-7.4 antibody (i.e. SEQ ID NO:2, 3, 4, 6, 7 and 8).

In some embodiments, the present invention further provides fragments said antibodies which include but are not limited to Fv, Fab, F(ab')2, Fab', dsFv, scFv, sc(Fv)2 and diabodies.

As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

As used herein, the term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

As used herein, the term "Fab'" refers to an antibody fragment having a molecular weight of about 50,000 and antigen binding activity, which is obtained by cutting a disulfide bond of the hinge region of the F(ab')2.

As used herein, a single chain Fv ("scFv") polypeptide is a covalently linked VH:VL heterodimer which is usually expressed from a gene fusion including VH and VL encoding genes linked by a peptide-encoding linker.

As used herein the term "dsFv" refers to a VH:VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

As used herein the term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The antibody of the present invention of the invention may be produced by any technique known in the art, such as, without limitation, any chemical, biological, genetic or enzymatic technique, either alone or in combination. For example, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid sequence encoding an antibody of the present invention. In some embodiments, the nucleic acid sequence encodes a heavy chain and/or a light chain of an antibody of the present invention.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculo virus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G1 1.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

In another particular embodiment, the method comprises the steps of: (i) culturing the hybridoma NTSp27-7.4 under conditions suitable to allow expression of NTSp27-7.4 antibody; and (ii) recovering the expressed antibody.

Antibodies of the present invention are suitably separated from the culture medium by conventional immunoglobulin purification procedures such as, for example, protein, A-Sepharose™, hydroxylapatite chromatography, gel electrophoresis, dialysis, or affinity chromatography.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (shitara K et al. 1994). Examples of tandem type humanized antibody expression vector include pKA TEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with Axl with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with Axl with a protease, pepsin. Also, the F(ab')2 can be produced by binding Fab' described below via a thioether bond or a disulfide bond.

The Fab' of the present invention can be obtained treating F(ab')2 which specifically reacts with Axl with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494). Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics. In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity. It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilcity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The antibodies may be assayed for specific binding by any method known in the art. Many different competitive binding assay format(s) can be used for epitope binning. The immunoassays which can be used include, but are not limited to, competitive assay systems using techniques such as western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al, eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the present invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present invention may be chemically modified (e.g., one or more chemical moieties can be attached to the antibody) or be modified to alter its glycosylation, again to alter one or more functional properties of the antibody.

For example, it will be appreciated that the affinity of antibodies provided by the present invention may be altered using any suitable method known in the art. The present invention therefore also relates to variants of the antibody molecules of the present invention, which have an improved affinity for neurotensine. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In some embodiments, the hinge region of CHI is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In some embodiments, the Fc hinge region of the antibody of the present invention is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In some embodiments, the antibody of the present invention is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al. In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcyRI, FcyRII, FcyRIII and FcRn have been mapped and variants with improved binding have been described (see Shields, R. L. et al, 2001 J. Biol. Chen. 276:6591-6604, WO2010106180).

In some embodiments, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn (297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyl-transferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the antibodies of the present invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono (CI—CIO) alkoxy- or aryloxy-poly ethylene glycol or polyethylene glycol-maleimide. In certain embodiments, the antibody to be pegylated is an aglycosylated antibody. Methods for pegylating proteins are known in the art and can be applied to the antibodies of the present invention. See for example, EP O 154 316 by Nishimura et al. and EP 0 401 384 by Ishikawa et al.

Another modification of the antibodies that is contemplated by the invention is a conjugate or a protein fusion of at least the antigen-binding region of the antibody of the present invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the present invention to proteins capable of binding to serum proteins, such human serum albumin to increase half-life of the resulting molecule. Such approach is for example described in Nygren et al, EP 0 486 525.

A further object of the present invention relates to a method of treating cancer in a subject in need thereof comprising administering the subject with a therapeutically effective amount of an antibody of the present invention.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued. Examples of cancers that may be treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyo sarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the patient suffers from a cancer deriving from epithelial origin. Examples of cancer types include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer, as well as subtypes of any of such cancers, including, but not limited to chemotherapy-resistant, platinum-resistant, advanced, refractory, and/or recurrent types thereof.

According to the invention the antibody of the present invention is administered to the patient with a therapeutically effective amount. By a "therapeutically effective amount" is meant a sufficient amount of the antibody of the present invention for the treatment of cancer at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the antibody of the present invention is used in combination with a chemotherapeutic agent. A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCINO, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea;

lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDSINEO, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

In some embodiments, the antibody is useful for restore the sensibility of cancer cells to chemotherapeutic agent, such as platinum-based antineoplastic drugs. Example of platinum-based antineoplastic drugs include cisplatin, carboplatin, oxaliplatin, satraplatin, picoplatin, nedaplatin, triplatin and lipoplatin.

In some embodiments, the antibody of the present invention is used in combination with a HER inhibitor.

As used herein the "HER" has its general meaning in the art and refers to a receptor protein tyrosine kinase which belongs to the HER receptor family and includes EGFR, HER2, HER3 and HER4 receptors. As used herein the terms "ErbB1," "HER1", "epidermal growth factor receptor" and "EGFR" are used interchangeably herein and refer to EGFR as disclosed, for example, in Carpenter et al. Ann. Rev. Biochem. 56:881-914 (1987), As used herein, the terms "ErbB2" and "HER2" are used interchangeably herein and refer to human HER2 protein described, for example, in Semba et al., PNAS (USA) 82:6497-6501 (1985) and Yamamoto et al. Nature 319:230-234 (1986) (Genebank accession number X03363). As used herein, the term "ErbB3" and "HER3" refer to the receptor polypeptide as disclosed, for example, in U.S. Pat. Nos. 5,183,884 and 5,480,968 as well as Kraus et al. PNAS (USA) 86:9193-9197 (1989). As used herein, the terms "ErbB4" and "HER4" refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993). By "HER ligand" is meant a polypeptide which binds to and/or activates a HER receptor.

As used herein the term "HER inhibitor" refers to an agent which interferes with HER activation or function. Examples of HER inhibitors include HER antibodies (e.g. EGFR, HER2, HER3, or HER4 antibodies); small organic molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Akt. Typically, the HER inhibitor is an antibody or small organic molecule which binds to a HER receptor. In some embodiments, the HER inhibitor is a "HER dimerization inhibitor" which is an agent which inhibits formation of a HER dimer or HER heterodimer.

In some embodiments, the HER inhibitor is an "anti-HER antibody" which is an antibody that binds to a HER receptor. In some embodiments, the anti-HER monoclonal antibody of the present invention is used to induce antibody dependent cellular cytotoxicity (ADCC) or complement dependent cytotoxicity (CDC) against HER-expressing cells. In another particular embodiment, the anti-HER antibody may be suitable for disturbing the expression of HER at the cell surface (e.g. by provoking internalization of HER) so that cell migration, cell proliferation and tumour growth of tumor cells will be limited or inhibited.

In some embodiments, the anti-HER antibody is an anti-HER monoclonal antibody-drug conjugate. An "anti-HER monoclonal antibody-drug conjugate" as used herein refers to an anti-HER monoclonal antibody according to the invention conjugated to a therapeutic agent. Such anti-HER monoclonal antibody-drug conjugates produce clinically beneficial effects on HER-expressing tumor cells when administered to a subject. In typical embodiments, an anti-HER monoclonal antibody is conjugated to a cytotoxic agent, such that the resulting antibody-drug conjugate exerts a cytotoxic or cytostatic effect on a HER-expressing tumor cell when taken up or internalized by the cell. Any cytotoxic agent well known by the skilled person may use. In some embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

Patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165,464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267,958, U.S. Pat. No. 6,685,940, U.S. Pat. No. 6,821,515, WO98/17797, U.S. Pat. No. 6,127,526, U.S. Pat. No. 6,333,398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat.

No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396, U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842, WO 03/86467, WO2013164689, WO2012059857.

In some embodiments, the HER inhibitor is a small organic molecule. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 da, and most preferably up to about 1000 Da.

In some embodiments, the HER inhibitor is tyrosine kinase inhibitor. A "tyrosine kinase inhibitor" is a molecule which inhibits tyrosine kinase activity of the HER receptor. Examples of such inhibitors include the small organic molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); non selective HER inhibitors such as Imatinib mesylate (Gleevec™); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino) phthalimide); tyrphostines containing nitrothiophene moieties; PD-0183805 (Warner-Lamber); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

In some embodiments, the HER inhibitor is an EGFR inhibitor. GFR inhibitors are well known in the art (Inhibitors of erbB-1 kinase; Expert Opinion on Therapeutic Patents December 2002, Vol. 12, No. 12, Pages 1903-1907, Susan E Kane. Cancer therapies targeted to the epidermal growth factor receptor and its family members. Expert Opinion on Therapeutic Patents February 2006, Vol. 16, No. 2, Pages 147-164. Peter Traxler Tyrosine kinase inhibitors in cancer treatment (Part II). Expert Opinion on Therapeutic Patents December 1998, Vol. 8, No. 12, Pages 1599-1625). Examples of such agents include antibodies and small organic molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small organic molecules that bind to EGFR include ZD1839 or Gefitinib (IRESSA™; Astra Zeneca); CP-358774 or erlotinib (TARCEVA™; Genentech/OSI); and AG1478, AG1571 (SU 5271; Sugen); EMD-7200. In some embodiments, the HER inhibitor is a small organic molecule pan-HER inhibitor such as dacomitinib (PF-00299804).

In some embodiments, the HER inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP261 13 (ALK and EGFR inhibitor). The inhibitors cetuximab, panitumumab, zalutumumab, nimotuzumab are monoclonal antibodies, erlotinib, gefitinib, lapatinib, neratinib, canertinib, vandetanib and afatinib are tyrosine kinase inhibitors.

The antibody of the present invention is typically combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The antibody can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active antibody in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: NTSp27-7.4 inhibits the proliferation inhibition of CHO over expressing NTSR1 induced by NTS or conditioned media from lung cancer cells overexpressing NTS. Results represent the mean±SEM of 3 independent experiments.

Figure 2:
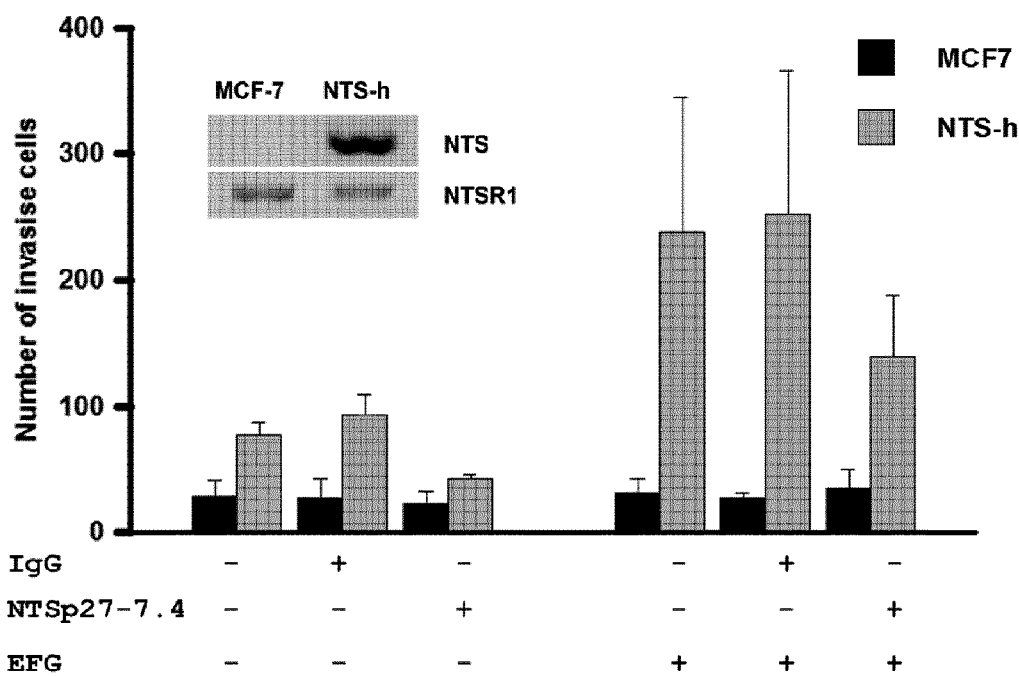

FIG. 2: NTSp27-7.4 inhibits the cellular invasion induced by EGF and NTS in breast cancer cells. Synergism between NTS and EGF on invasion in a collagen 1 invasion assay of MCF-7 and NTS-1 cells. Cells were seeded on the top of a collagen type 1 gel and treated with EGF (100 ng/mL). Results represent the mean±SEM of 3 experiments. Inset, NTS and NTSR1 transcript analysis from 200 ng of MCF-7, and NTS-h, total RNA.

Figure 3A:
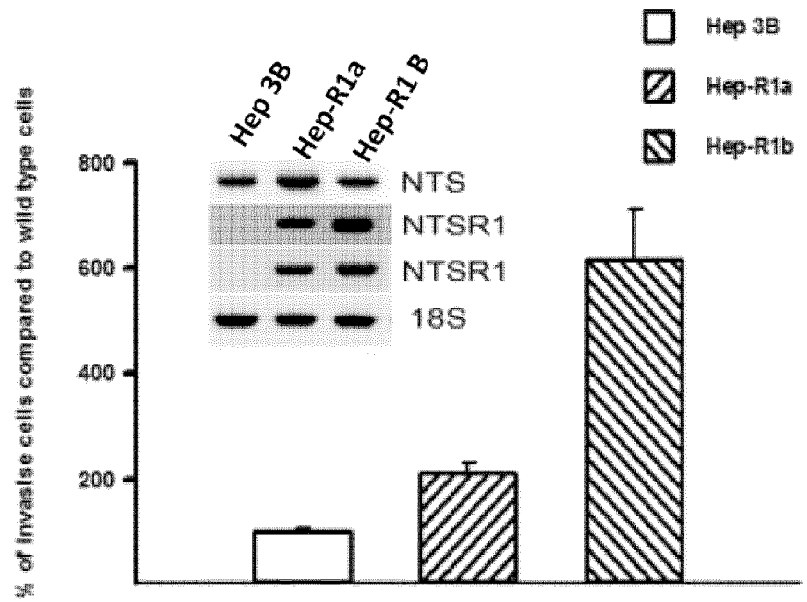
Figure 3B:
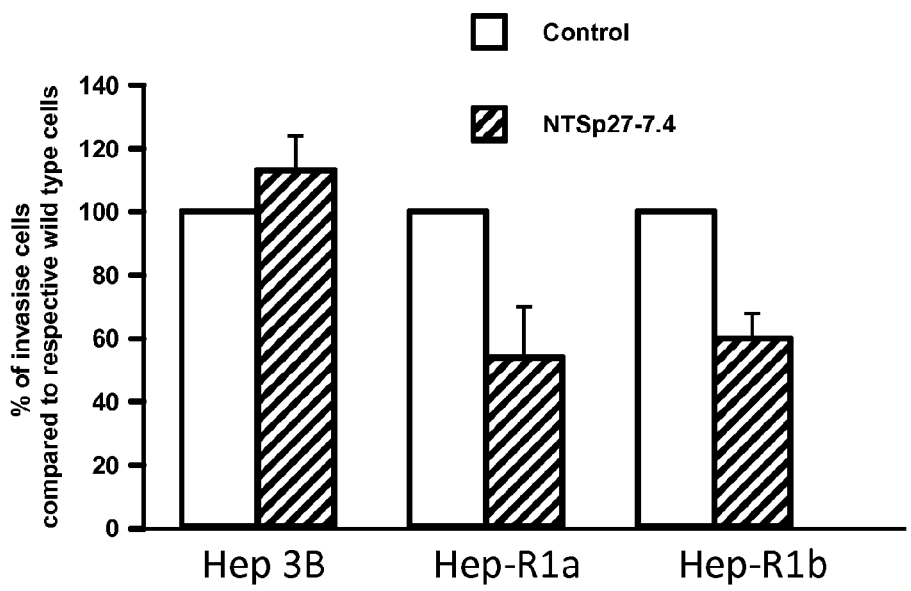

FIG. 3. NTSp27-7.4 inhibits the cellular invasion induced by NTS in Hepatocellular carcinoma. A) Migration in a collagen 1 invasion assay of Hep 3B, HepR1a, and HepR2b cells. Results represent the mean±SEM of 3 experiments. Results are expressed as a % on invasive cells of control cells, Hep3B. Inset, NTS and NTSR1 transcript analysis from 200 ng of Hep 3B, HepR1a, and HepR2b total RNA. B) Migration in a collagen type 1 invasion assay of Hep 3B, HepR1a, and HepR2b cells in a presence of 3.75 µg/ml of purified NTSp27-7.4 or mouse IgG. Results represent the mean±SEM of 3 experiments. Results are expressed as a % on invasive cells of respective control cells.

FIG. 4. NTSp27-7.4 inhibits experimental tumor growth generated by lung cancer cell lines. A) LNM-R or R-SI NTSR1 cells (LNM-R expressing sh-RNA for NTSR1) were injected into the left and the right flank of the mice, respectively. Here is shown an example of a mouse from each group after 15 days of treatment. B) Tumor growth generated by LNM-R cells (left flank) xenografted into nude mice and treated for 15 days with PBS, or 15 mg/kg NTSp27-7.4. At day one, 10, and 8 mice were randomized on LNM-R tumors size reaching approximately 40 mm3 for control and NTSp27-7.4 group, respectively. Mice were treated every other day and measured every day. C) Tumor growth generated by R-SI NTSR1 cells (right flank) xenografted into the same mice. D and E) Tumor growth rate from day one generated by LNM-R cells (left flank) and R-SI NTSR1 cells (right flank).

FIG. 5. NTSp27-7.4 inhibits experimental tumor growth generated by breast cancer cell lines. Tumor growth generated by MDA-MB 231 cells (left flank) (A), and MDA Si2 cells (right flank) (B), and treated for 24 days with PBS, or 15 mg/kg NTSp26-8.2. At day one, 7, and 6 mice were randomized for the size of MDA-MB231 tumors size; reaching approximately 50 mm3. Mice were treated and measured every other day.

FIG. 6. NTSp27-7.4 restores cisplatin response to lung cancer cell lines expressing NTS and NTSR1. A) LNM-R or R-SI NTSR1 cells (LNM-R expressing sh-RNA for NTSR1) were injected into the left and the right flanks of the mice, respectively; Mice were treated with PBS, or 15 mg/kg NTSp27-7.4 every other day and/or with cisplatin 1 mg/kg day 1, 3, 5, 7, 15, 17, and 19. At day one, 9 and 8 mice were randomized for the size of the LNM-R tumors; reaching approximately 95 mm3 on average. Mice were treated every other day and measured every day. B) Tumor growth rate from day one generated by R-SI NTSR1 cells (right flank).

FIG. 7. NTSp27-7.4 induces apoptosis in ovarian cancer cell lines expressing NTS and NTSR1. A) NTS, NTSR2, and NTSR1 transcript analysis from 100 ng of A2780 and SKOV3 total RNA. B) The Annexin-V-FITC Apoptosis Detection Kit (Roche) was used to detect apoptosis by flow cytometry. (Left) Example of FACS analysis on cells treated or not with 50 µg/ml of NTS p27-7.4 for 24 h. (Right) Apoptosis levels of NTS p27-7.4 treated cells presented as the fold increase relative to the apoptosis of untreated cells n=3.

Figure 8:
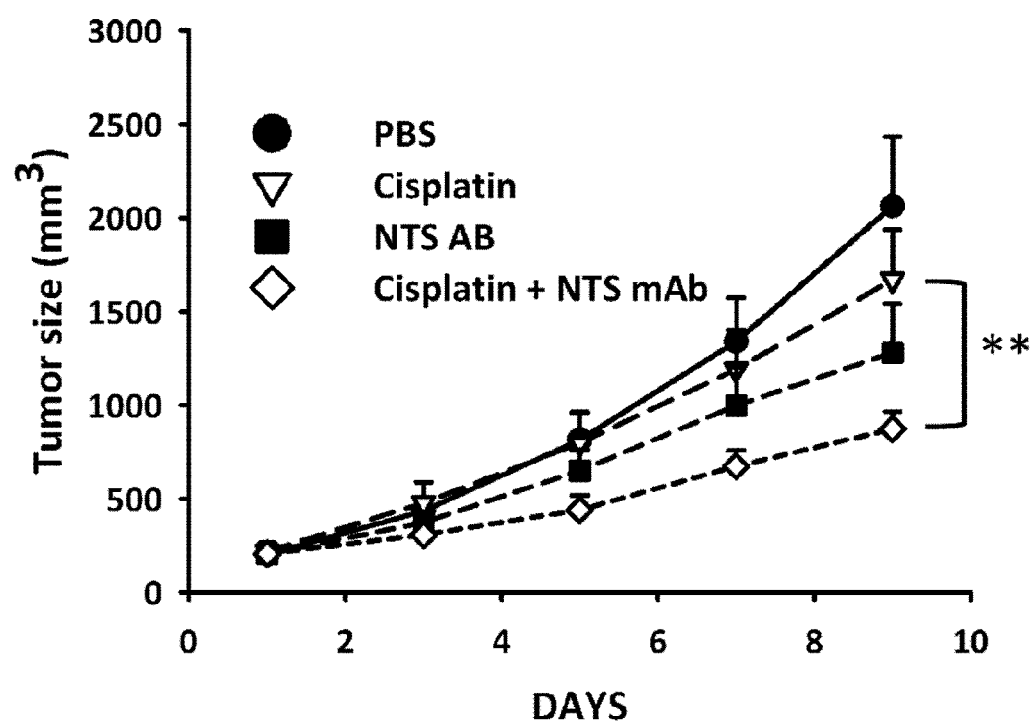

FIG. 8. NTSp27-7.4 restores cisplatin response to ovarian cancer cell lines expressing NTS and NTSR1. 3 million A2780 cells were injected into mice. When tumors generated by A2780 reached an average volume of 200 mm$^3$, mice were randomized into 4 groups. Mice were treated with PBS, or 15 mg/kg NTSp27-7.4 every other day and/or with cisplatin 1 mg/kg day at 1, 3, 5, and 7 days. Results are the mean of 8 to 12 mice performed in two different independent experiments.

EXAMPLES

Example 1: Cloning and Sequencing of Antibody Variable Regions

Step 0: Peptide Synthesis and Conjugation

In order to inhibit NTS oncogenic action, we produced NTS monoclonal antibody directed against NTS long fragment (SEQ ID NO:9: mmagmkiqlv cmlllafssw slcsdseeem kaleadfltn mhtskiskah vpswkmtlln vcslvnnlns paeetgevhe eelvarrklp taldgfslea mltiyqlhki chsrafqhwe liqedildtg ndkngkeevi krkipyilkr qlyenkprrp yilkrdsyyy). The antigen peptide sequence chosen was SEQ ID NO:10 (CQLYENK-PRRPYIL-amide MW 1792.2). 1. Peptide synthesis was controlled by MS and HPLC. The peptide used was the lyophilised form as TFA-salt and conjugated with BSA.

Step 1 Immunisation 5 mice were immunized with the antigen.

| | OD$_{405\ nm}$ after 15 min incubation with the substrate. The ELISA plates were coated with 50 µl/well p12027-BSA-conjugate (concentration 4 µg/ml). | | | | | |
|---|---|---|---|---|---|---|
| dilution of antiserum | mouse 1 | mouse 2 | mouse 3 | mouse 4 | mouse 5 | normal serum |
| 1:100 | 2.282 | 2.236 | 2.110 | 2.262 | 2.364 | 0.019 |
| 1:200 | 2.278 | 2.260 | 2.207 | 2.281 | 2.332 | 0.015 |
| 1:400 | 2.404 | 2.372 | 2.346 | 2.404 | 2.262 | 0.011 |
| 1:800 | 2.423 | 2.381 | 2.488 | 2.475 | 2.292 | 0.009 |
| 1:1600 | 2.306 | 2.236 | 2.400 | 2.391 | 2.016 | 0.015 |
| 1:3200 | 2.058 | 2.018 | 2.285 | 2.199 | 1.726 | 0.008 |
| 1:6400 | 1.668 | 1.620 | 1.927 | 1.866 | 1.286 | 0.000 |
| 1:12800 | 1.198 | 1.183 | 1.451 | 1.426 | 0.885 | 0.000 |

The functional test was inhibition of morphological changes of CHO stably overexpressing NTSR1 and induced by $10^{-8}$ or $10^{-7}$ M JMV449 a weekly degradable NTS agonist, or the culture medium of LNM35 cells expressing NTS and NTSR1. The results were the following ones: Serum from mice #3 and 5 inhibited the morphology changes by 15% and 10% respectively, and the mouse #1 only by 5% compare to preimmune serum. The serum of the mice 2 and 4 did not inhibit the morphology changes.

Step 2 Fusion:

The mouse 3 and 5 were selected. Two clones were positive after the first cloning test. Clones 1-5, 7-4 were tested.

Two test were performed 1) the NTS induced CHO NTSR1 morphology changes test and 2) the invasion test on type I collagen matrices of MCF-7 cell overexpressing NTS. The experiment was repeated twice.

The clone 1.5 inhibited the NTS effect in both tests from 50 to 60%, and the clone 7.4 inhibited the NTS effect in both tests from 10 to 20% according to the control.

Unfortunately the clone 1.5 was very unstable and got lost.

Step 3: Final Selection

Finally, clone 7.4 (i.e. NTSp27-7.4) hybridoma was selected. Antibody was purified and tested in proliferation assay of CHO NTSR1, invasion assay of breast cancer cells expressing of not NTS, hepatocellular carcinoma expressing or not NTSR1. NTSp27-7.4 was also tested on tumor growth of breast and lung cancer cells, and on the response to cisplatin in lung cancer model. (See result section).

Step 4: Cloning and Sequencing:

Total RNA was prepared from $2 \times 10^7$ of the cells from the first tube provided for each hybridoma using the Qiagen RNeasy mini kit (Cat No: 74104). RNA was eluted in 60 μL water and checked on a 1.2% agarose gel alongside Qarta Bio 1 Kb Markers (cat: M-DNA-1 Kb). $V_H$ and $V_K$ cDNAs were prepared using reverse transcriptase with IgG and kappa constant region primers. The first strand cDNAs were amplified by PCR using a large set of signal sequence primers. The amplified DNAs were gel-purified and cloned into the vector pGem T Easy (Promega). The $V_H$ and $V_K$ clones obtained were screened for inserts of the expected size. The DNA sequence of selected clones was determined in both directions by automated DNA sequencing. The locations of the CDRs in the sequences were determined with reference to other antibody sequences (Kabat E A et al., 1991)

A single productive $V_K$ sequence was identified in ten clones (eight independent). The sequences were identical apart from a single base change in one clone at position 33 and a single base change in another clone at position 315. A non-productive aberrant $V_K$ with an error in V-J joining and the aberrant $V_K$ sequence that arises from the fusion partner were also found. The deduced protein sequence with CDRs annotated is shown in Table A.

A single $V_H$ sequence was identified. Identical sequence was found in six independent clones apart from two single base changes at residues 22 and 243 in one clone, a single base change in one clone at position 103 and a single base change in another clone at position 261. The deduced protein sequence with CDRs annotated is shown in Table A.

TABLE A

Sequences of NTSp27-7.4 antibody

| Domain | Sequences |
|---|---|
| VH | DVKLVESGGGLVKLGGSLKLSCAASGFTFSGYYMSWVRQTP EKRLELVAAINNYGDNTNYPDTVKGRFSVSRDNAKNTLYLE MNSLKSEDTALYYCARLANYANQRGAMDYWGQGTSVTSS (SEQ ID NO: 1) |
| H-CDR1 | GFTFSGYYMS (SEQ ID NO: 2) |
| H-CDR2 | AINNYGDNTNYPDTVKG (SEQ ID NO: 3) |
| H-CDR3 | LANYANQRGAMDY (SEQ ID NO: 4) |
| VL | DIQMTHTTSSLSASLGDRVTISCRASQDIANYLNWYQQKPD GTVTLLIYYTSRLHSGVPSRFSGSGSGTDYSLTINNLDQED IATYFCQQGYTLPPTFGGGTKLEIK (SEQ ID NO: 5) |
| L-CDR1 | RASQDIANYLN (SEQ ID NO: 6) |
| L-CDR2 | YTSRLHS (SEQ ID NO: 7) |
| L-CDR3 | QQGYTLPPT (SEQ ID NO: 8) |

Example 2: Functional Assays

Material & Methods:

Cell Proliferation 20 000 CHO-NTSR1 cells were seeded in 48 well dishes, in 200 ul media 10% with FCS. The next day the cells were treated with $10^{-7}$ M Neurotensin or ½ LNM-R conditioned media which were pre-incubated for 2 h at room temperature in the presence or not of 2.8 μg antibody P27-7.4. The conditioned media was prepared as follows. 3 million LNM-R cells were seeded in 75 cm² flask in media with 10% FCS. Cells were grown for 24 h, media were removed, and 10 ml serum free media were added. The media were collected and centrifuged 5 mins at 500 g after 48 h. The supernatant was aliquoted and freeze at −20° C. until used. Cells were treated for 40 h in 200 μl media with 2.5% FCS. Cellular proliferation was evaluated by counting using Beckman Coulter's cell counting.

Invasion Assay

The cell culture insert (8 μm, Beckton Dickinson®) was coated with type I collagen (100 μl/well, $4 \times 10^2$ μg/ml, Sigma®) at 37° C. 24 h before the assay. 1 million MCF, NTS-h, Hep 3B, HepR1a, and HepR2b cells were seeded in the insert with 250 μl of serum free medium in presence or absence of 7 μg antibodies NTSp27-7.4. Outside the insert, 750 μl medium with 10% FCS was added in the well as chemoattractant. After 48 h of incubation, the non-invading cells and collagen are removed from the upper surface of the membrane by scrubbing with a cotton swab. Invading cells (those adhering to the bottom surface of the membrane) were fixed and stained with the Kwif diff stain kit(Thermo®) and the number of stained cells were counted with an inverted microscope at 200× magnification.

Tumor Xenografts $1 \times 10^6$ LNM-R cells and $1 \times 10^6$ R-SI NTSR1 were subcutaneously inoculated in NMRI nu/nu mice, LNM-R in the left flank and R-SI NTSR1 in the right flank. When tumors generated by LNM-R reached an average volume of 40 mm³, mice were randomized in 2 groups, then administered antibody NTSpP27-7.4 (i.p. every other day, 15 mg/kg) for total 8 times. PBS was used as the vehicle control. The volume of tumor was measured daily.

$3 \times 10^6$ MDA-MB 231 cells and $3 \times 10^6$ MDA si2 were subcutaneously inoculated in 100 μl of MATRIGEL® (a gelatinous protein mixture) the left flank and the right flank of the NMRI nu/nu mice, respectively. When tumors generated by MDA reached an average volume of 50 mm³, mice were randomized in 2 groups, then administered antibody NTSpP27-7.4 (i.p. every other day, 15 mg/kg) for total 12 times. PBS was used as the vehicle control.

Cisplatin test, $1 \times 10^6$ LNM-R cells and $1 \times 10^6$ R-SI NTSR1 were subcutaneously inoculated in NMRI nu/nu mice, LNM-R in the left flank and R-SI NTSR1 in the right flank. When tumors generated by LNM-R reached an average volume of 95 mm³, mice were randomized in 5 groups of 8 to 10 mice. Group 1 was administered with PBS, group 2 with antibody NTSp27-7.4 (i.p. every other day, 15 mg/kg) for total of 13 times and group 3 with mouse IgG (i.p. every other day, 15 mg/kg). Group 4 was administered with PBS and cisplatin (1 mg/kg at day 1,3 5 7, 15, 17, and 19) and groups 5 with antibody NTSp27-7.4 (i.p. every other day, 15 mg/kg) and cisplatin (1 mg/kg at day 1,3 5 7, 15, 17, and 19). The volume of tumor was measured every other day.

FACS Analysis

The Annexin-V-FITC Apoptosis Detection Kit (Roche) was used to detect apoptosis by flow cytometry. Cells were exposed or not to 50 µg/ml of NTS p27-7.4 in 0.5% FCS for 24 h. Cells were harvested by accutase (including detached cells), and detected in a Flow Cytometer (BD LSR II).

A2780 cells (3×10⁶) cells were combined with 50 PBS and 50 µl MATRIGEL® (a gelatinous protein mixture), then injected subcutaneously into the right hind leg of 4 week old female NMRI-Nude Foxn1 mice. Treatment started when tumors reached approximately 200 mm3. Tumor volume was calculated every two days by using the following equation: tumor volume (mm3)=4/3×π×(length/2)×(width/2)×(height/2). After treatment, the mice were sacrificed and tumors were fixed in formalin.

Results:

Neutralization of NTS Induced Proliferation Inhibition of CHO Over Expressing NTSR1.

LNM-R cells expressed NTS and NTSR1. NTS is released in the media and was assay by radioimmunoassay. Culture medium (CM) of LNM-R cells contained 76.4±10.3, 153.2±25.3, and 624.3±81.8 fmol/mL of NTS corresponding to 14, 48, and 72 hours of culture, respectively. When CHO NTSR1 overexpressing cells are exposed to NTS, cells change shape which induced a decrease in proliferation rate. In FIG. 1, cell growth is reduced by 60% when cells are treated by NTS or CM, when the purified monoclonal antibody NTSp27-7.4 is added to the media this cellular growth inhibition is reduced to 30% and 26%, for NTS or CM treated cells, respectively.

Neutralization of NTS Induced Invasion of Breast Cancer Cell Expressing NTS.

The breast cancer cell line, MCF-7, constitutively expressing NTSR1 was stably transfected with the neurotensin full length coding sequence. An overexpressing NTS clone, NTS-h, was selected (FIG. 2 inset). The invasiveness properties of NTS-h, was studied using a 3 dimensional collagen invasion assay. The ectopic NTS expression of MCF-7 cells induced a small increase in invasiveness properties. EGF-induced invasion was tripled in NTS-overexpressing cells as compared to MCF-7 (FIG. 2). The induction of invasiveness induced or not by EGF was inhibited by NTSp27-7.4 only in the NTS-overexpressing clones. This confirms the neutralizing properties of the NTS monoclonal antibody NTSp27-7.4.

Neutralization of NTS Induced Invasion of Liver Cancer Cell Expressing NTSR1.

Hep3B is a Hepatocellular carcinoma which constitutively expresses NTS, but not NTSR1. The Hep3B cells were stably transfected with NTSR1 coding sequence and two clones were selected, Hep-R1a and Hep-R1b (FIG. 3A inset). The invasiveness properties of cells were studied using a 3 dimensional collagen invasion assay. The ectopic expression of NTSR1 largely increased the invasive properties of the cells as shown in FIG. 3A. When cells were exposed to NTSp27-7.4, the invasive rate of the cells expressing NTS and NTSR1 was reduced, and more drastic for the cells for which the increase of invasive rate was moderate, Hep-R1a. Both results confirm the neutralizing properties of this NTS antibody on cell invasiveness.

NTSp27-7.4 Reduced Tumor Growth Specifically in Tumor Expressing NTS and NSTR1.

Figure 4A:
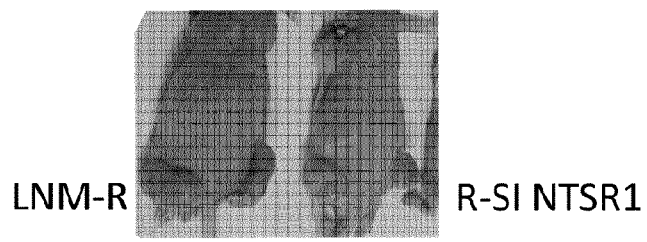
Figure 4B:
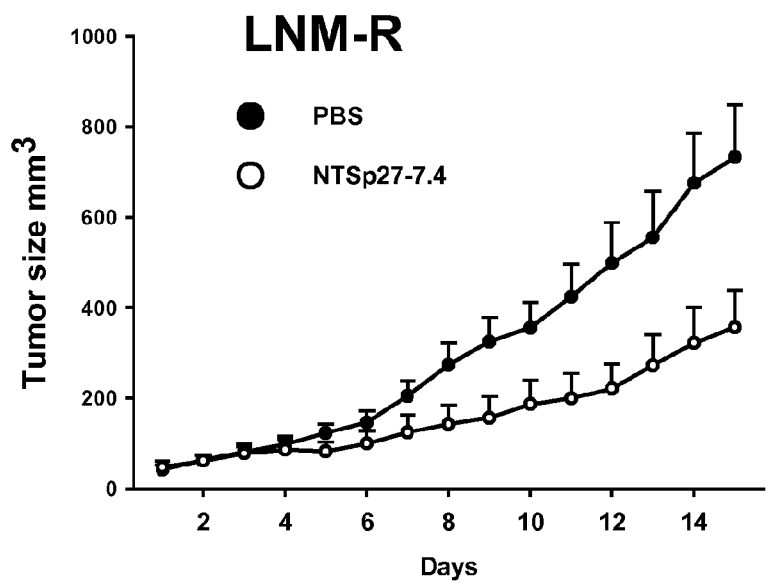
Figure 4C:
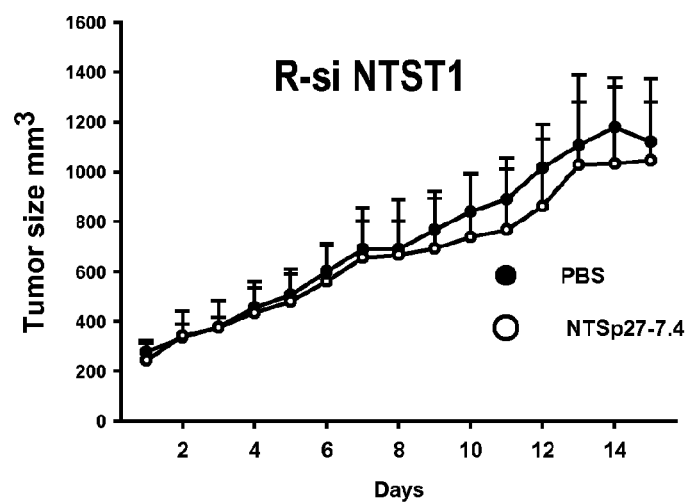
Figure 4D:
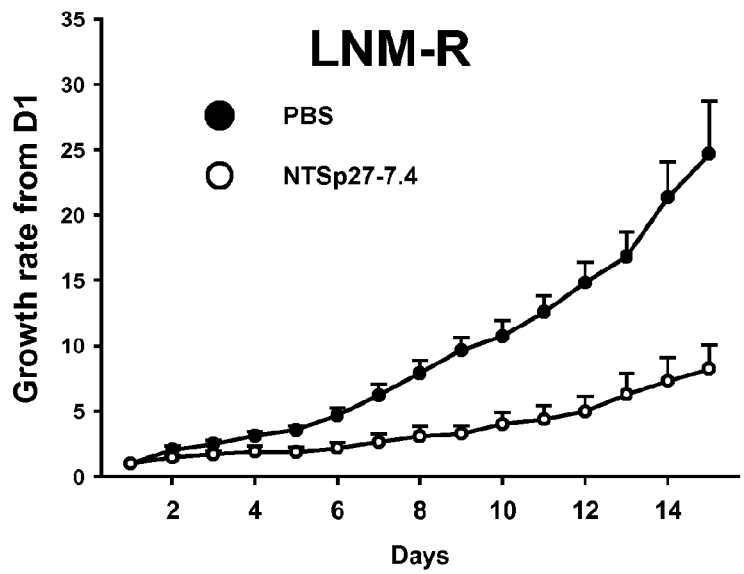
Figure 4E:
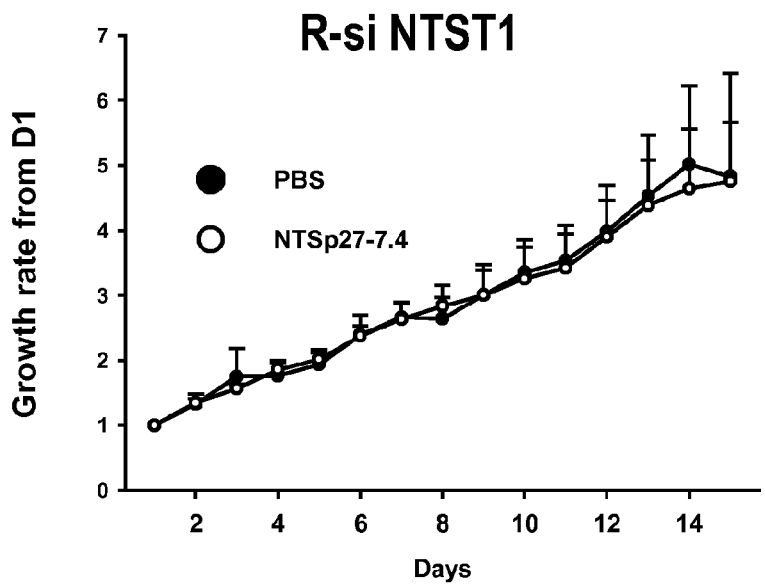

The efficiency of NTSp27-7.4 to decrease tumor growth was tested on lung cancer experimental tumors generated by cells expressing LNM-R cells, expressing NTS and NTSR1 or R-SI NTSR1 cells which express only NTS. The R-SI NTSR1 cells are a clone obtained from LNM-R and stably transfected with NTSR1 Sh RNA. Mice were grafted with both cell lines. LNM-R cells on the left flank and R-SI NTSR1 cells on the right flank (FIG. 4A). Mice were randomized with LNM-R tumors 42±11 mm³ and 43±8 mm³ for PBS and NTSp27-7.4 treated group, respectively. The tumor size of animals treated with the NTSp27-7.4 was 2.6 times smaller as compared to controls (FIG. 4B). The doubling time after 16 days of treatment was 3.43±0.34 and 5.11±0.38 days for control and NTSp27-7.4 treated animals, respectively. The growth from D1 was 24.68±4.05 fold for PBS treated animals and only of 8.22±1.84 for NTSp27-7.4 treated animals (FIG. 4D). The specificity and the efficiency of the antibody was confirmed when the tumors carrying the non-expressing NTSR1, in the same mice, were analyzed. For R-I NTSR1 tumors, the size of the tumor and the growth rate were not different whether the mice were treated with PBS or NTSp27-7.4 (FIGS. 4C and 4E).

Figure 5A:
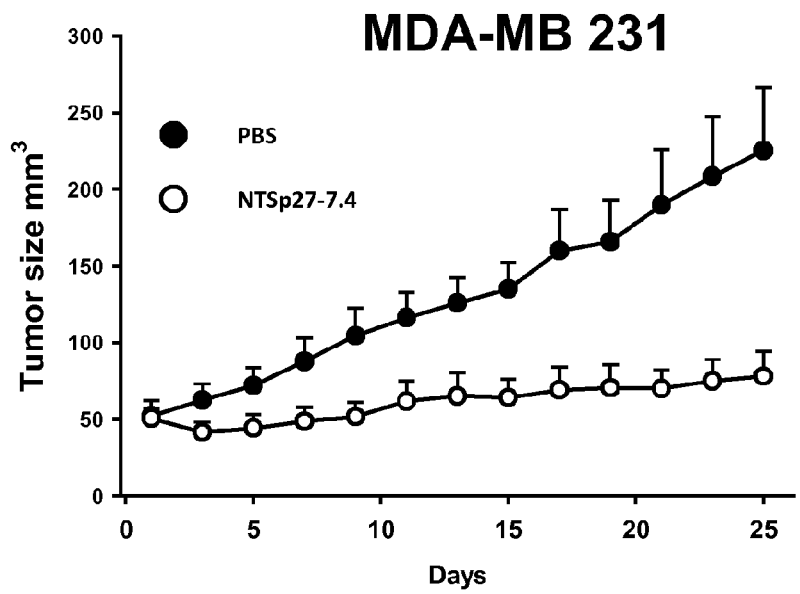
Figure 5B:
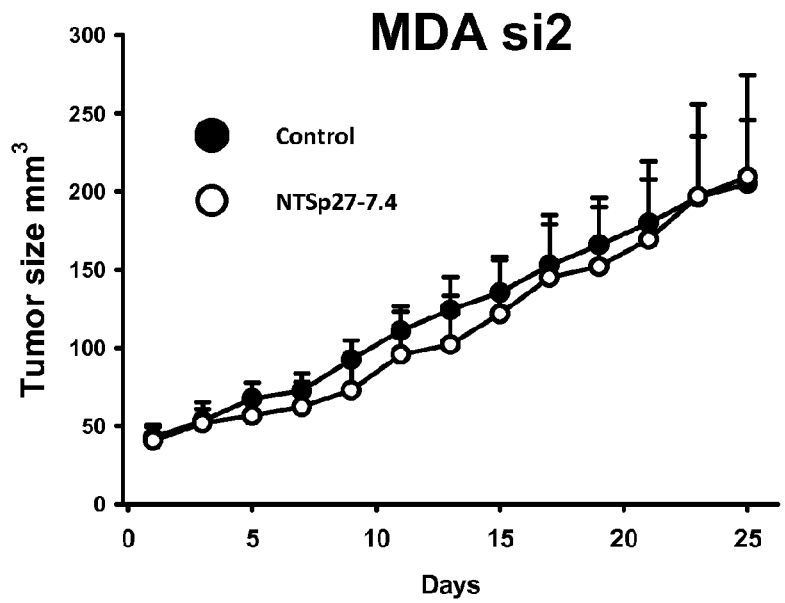

In the same vein NTSp27-7.4 was also shown to efficiently reduce tumor growth generated by breast cancer cells. MDA-MD 231 expressing NTS and NTSR1 and its subclone MDA Si2 stably transfected with sh NSTR1, were xenografted on the flank on mice. MDA-MD 231 cells on the left flank and MDA Si2 cells on the right flank. MDA Si2 cells were injected a few days before MDA MD 231. Mice were randomized with MDA-MB231 tumors, as follows 52±10 mm³ for control group and 50.7±6.3 mm³ for NTSp27-7.4 group. FIG. 5A shows a strong reduction of MDA-MB231 tumor growth from cells by NTSp27-7.4 as compared to PBS treated animals. The growth rate from D1 was 4.4±0.33 fold for PBS treated animals and only of 1.5±0.1 for NTSp27-7.4 treated animals. The doubling time after 24 days of treatment was 11.63±1 and 52.8±17.6 days for control and NTSp27-7.4 treated animals, respectively. The same parameters analyzed on the MDA Si2 tumors (NTSR1−) showed no difference between the tumor sizes (FIG. 5B), the growth rate and the doubling time.

NTSp27-7.4 Restores Cisplatin Response

The ability of NTSp27-7.4 to restore cisplatin response was tested on lung cancer experimental tumors generated by cells expressing LNM-R cells, expressing NTS and NTSR1 or R-SI NTSR1 cells which express only NTS. Mice were grafted with both cell lines. LNM-R cells on the left flank and R-SI NTSR1 cells on the right flank.

Figure 6A:
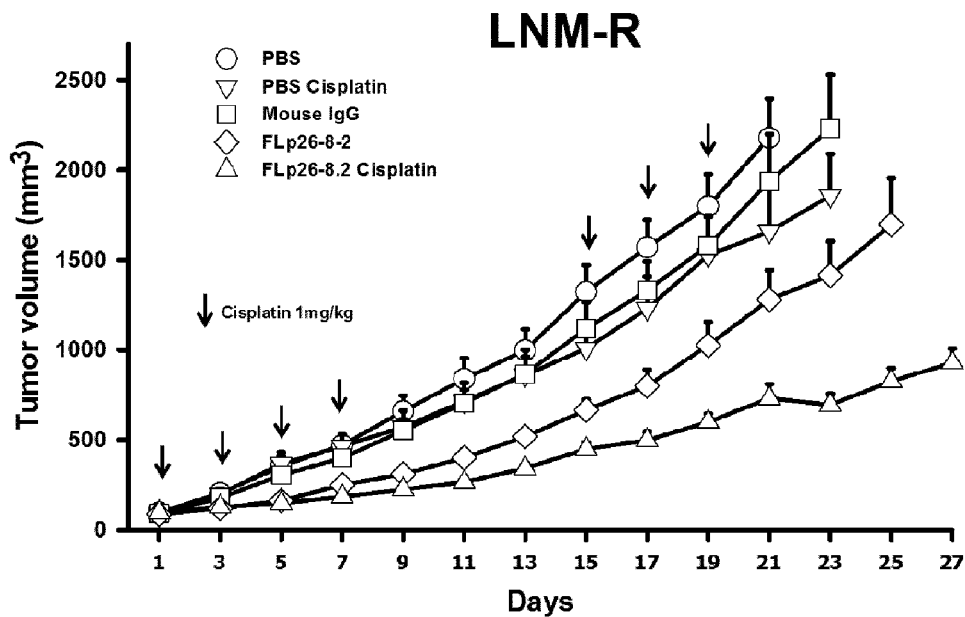

Mice were randomized with LNM-R tumors 96.3±18.5, 96.4±14.2, 91.3±14.9, 92.9±10.6 and 91.4±10.1 mm³ for PBS, NTSp27-7.4, PBS and cisplatin, NTSp27-7.4 and cisplatin, or Mouse IgG treated group, respectively. Because the large size of the tumors the experiment was stopped after 21 for the control group, 23 days for IgG and PBS cisplatin group, 25 days for NTSp27-7.4 group and 27 days for NTSp27-7.4 and cisplatin group. For LNM-R tumors, the size or the tumor with time are shown in FIG. 6A. As R-SI NTSR1 tumors could not be randomized, the result are presented as the growth ratio to D1 (FIG. 6B).

LNM-R tumor growth rate were not altered by cisplatin treatment or purified IgG treatment, as compared to PBS treated mice (FIG. 6A). As previously shown, when animals are treated with NTSp27-7.4 the LNM-R tumor size is smaller. The size tumor is stabilized when animals are treated with NTSp27-7.4 and cisplatin (FIG. 6A).

Figure 6B:
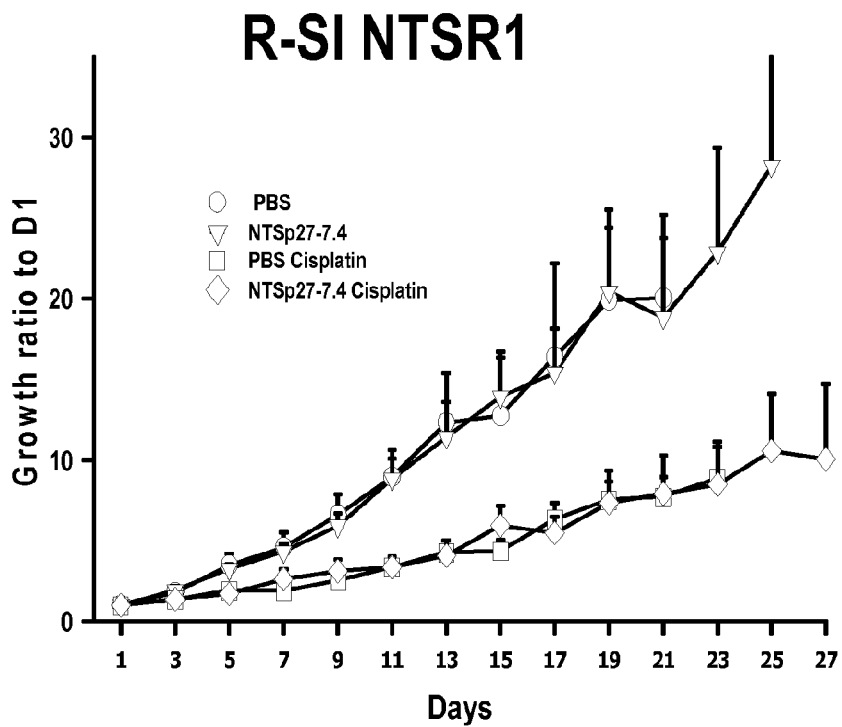

The R-SI NTSR1 tumor size is decreased when animals are treated with cisplatin, indicating that NTS/NTSR1 complex is implicated in the cellular resistance to cisplatin (FIG. 6B). As expected, combined treatment with NTSp27-7.4 do not change the tumor growth rate.

Neutralization of NTS Induced Apoptosis of Ovarian Cancer Cell Expressing NTSR1.

Figure 7A:
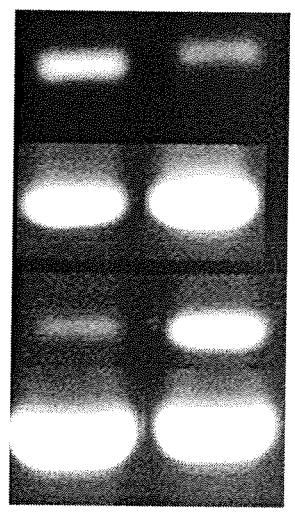
Figure 7B:
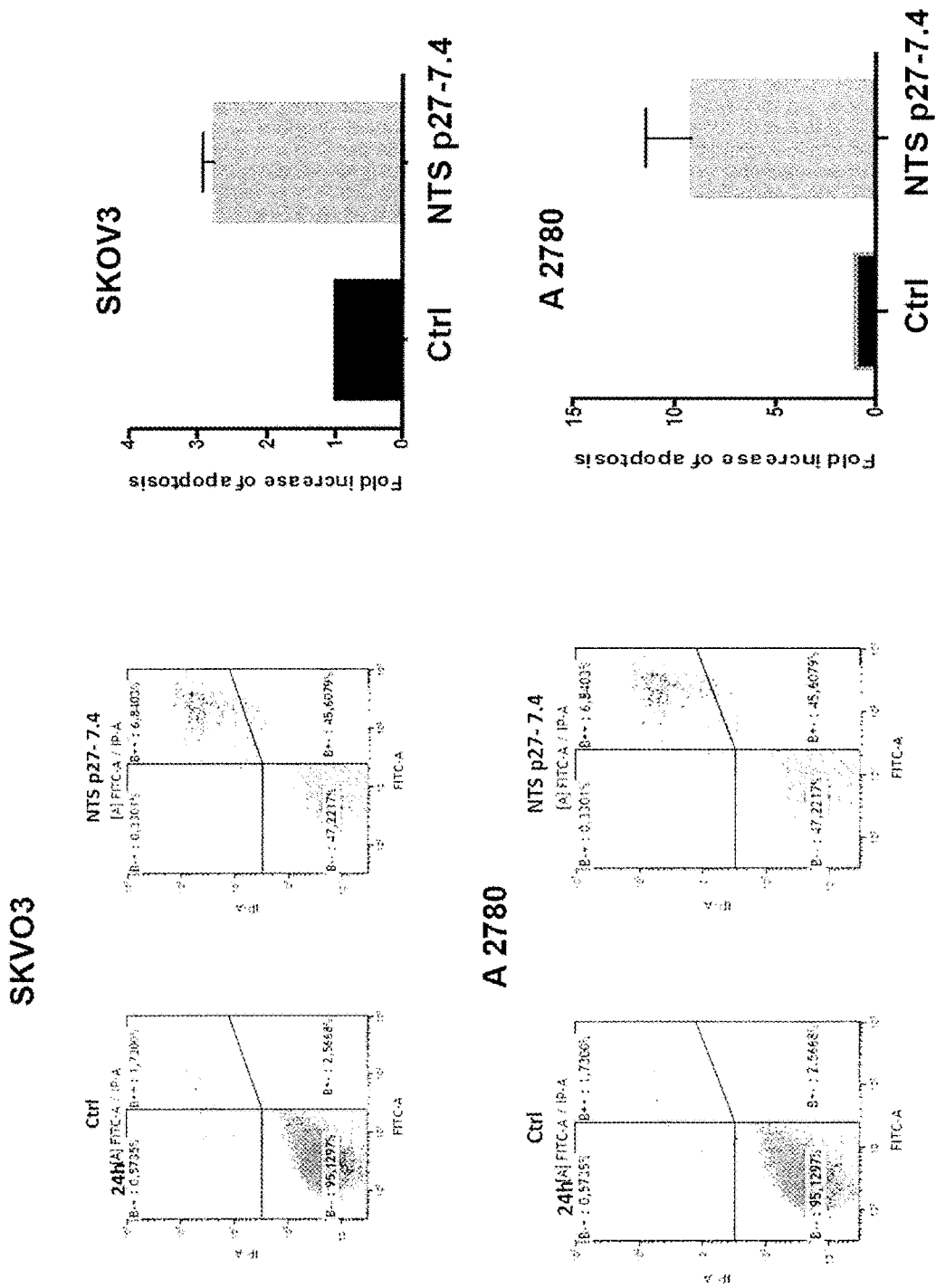

A 2780 and SKOV3 are human ovarian carcinoma cells which constitutively express NTS, NTSR1 and NTSR2 as shown in FIG. 7A. Apoptosis induced by NTS antibody was by Annexin V-FITC/PI staining after treating cells with NTS p27-7.4 for 24 hours, followed by fluorescence activated cell sorting analysis. Gate settings distinguish between living (bottom left), necrotic (top left), early apoptotic (bottom right), and late apoptotic (top right) cells. The two-dimensional dot plots show an increase of the fluorescent dots in early apoptotic, and late apoptotic cells in both cell lines. Levels of NTS p27-7.4 induced apoptosis presented as fold increase relative to control cells is 2.5% and 8.2% for A2780 and SKOV3 cells, respectively (FIG. 7B).

The ability of NTSp27-7.4 to restore cisplatin response was tested on ovarian cancer experimental tumors generated by A 2780 cells, expressing NTS and NTSR1. Mice were randomized as follows 201.3±33.8, 217.15±47.6, 203.5±32.6, and 205.9±46 5 mm$^3$ for PBS, NTSp27-7.4, PBS and cisplatin, or NTSp27-7.4 and cisplatin, treated group, respectively. A2780 tumor growth rates were slightly but not significantly altered by cisplatin treatment as compared to PBS treated mice (FIG. 8). When animals are treated with NTSp27-7.4 the A2780 tumor size was smaller 2062±371.5 mm$^3$, and 1280±262.0 mm$^3$ for PBS and NTSp27-7.4 treated group, respectively, p=0.054 vs PBS group. The tumor growth rate is more reduced when animals are treated with NTS p27-7.4 and cisplatin to 870.75±92.8 mm$^3$ p=0.0058 vs cisplatin group (FIG. 8).

In conclusion, the treatments with NTSp27-7.4 restore the sensitivity to cisplatin of cells expressing NTS and NTSR1, and can be proposed to patients with NSLCL and Ovarian cancer expressing high levels of NTSR1.

REFERENCES

Throughout this application, various references describe the state of the art to which this invention pertains. The disclosures of these references are hereby incorporated by reference into the present disclosure.

1. Carraway, R. & Leeman, S. E. (1973) J. Biol. Chem. 248, 6854-6861.
2. Rosell, S. (1980) Soc. Gen. Physiol Ser. 35, 147-162.
3. Rosell, S., Al-Saffar, A., & Thor, K. (1984) Scand. J. Gastroenterol. Suppl 96, 69-75.
4. Vincent, J. P., Mazella, J., & Kitabgi, P. (1999) Trends Pharmacol. Sci. 20, 302-309.
5. Thomas, R. P., Hellmich, M. R., Townsend, C. M., Jr., & Evers, B. M. (2003) Endocr. Rev. 24, 571-599.
6. Wu, Z., Martinez-Fong, D., Tredaniel, J., & Forgez, P. (2012) Front Endocrinol. (Lausanne) 3, 184.
7. Dupouy, S., Mourra, N., Doan, V. K., Gompel, A., Alifano, M., & Forgez, P. (2011) Biochimie 93, 1369-1378.
8. Alifano, M., Souaze, F., Dupouy, S., Camilleri-Broet, S., Younes, M., hmed-Zaid, S. M., Takahashi, T., Cancellieri, A., Damiani, S., Boaron, M. et al. (2010) Clin. Cancer Res. 16, 4401-4410.
9. Dupouy, S., Viardot-Foucault, V., Alifano, M., Souaze, F., Plu-Bureau, Chaouat, M., Lavaur, A., Hugol, D., Gespach, C., Gompel, A. et al. (2009) PLoS. One. 4, e4223.
10. Shimizu, S., Tsukada, J., Sugimoto, T., Kikkawa, N., Sasaki, K., Chazono, H., Hanazawa, T., Okamoto, Y., & Seki, N. (2008) Int. J. Cancer 123, 1816-1823.
11. Guha, S., Rey, O., & Rozengurt, E. (2002) Cancer Res. 62, 1632-1640.
12. Heakal, Y., Woll, M. P., Fox, T., Seaton, K., Levenson, R., & Kester, M. (2011) Cancer Biol. Ther. 12, 427-435.
13. Ishizuka, J., Townsend, C. M., Jr., & Thompson, J. C. (1993) Ann. Surg. 217, 439-445.
14. Somai, S., Gompel, A., Rostene, W., & Forgez, P. (2002) Biochem. Biophys. Res. Commun. 295, 482-488.
15. Souaze, F., Dupouy, S., Viardot-Foucault, V., Bruyneel, E., Attoub, S., Gespach, C., Gompel, A., & Forgez, P. (2006) Cancer Res. 66, 6243-6249.
16. Iwase, K., Evers, B. M., Hellmich, M. R., Kim, H. J., Higashide, S., Gully, D., & Townsend, C. M., Jr. (1996) Surg. Oncol. 5, 245-251.
17. Yoshinaga, K., Evers, B. M., Izukura, M., Parekh, D., Uchida, T., Townsend, C. M., Jr., & Thompson, J. C. (1992) Surg. Oncol. 1, 127-134.
18. Nakaizumi, A., Uehara, H., Baba, M., Iishi, H., & Tatsuta, M. (1996) Cancer Lett. 110, 57-61.
19. Tatsuta, M., Iishi, H., Baba, M., & Nakaizumi, A. (1991) Int. J. Cancer 47, 408-412.
20. Servotte, S., Camby, I., Debeir, O., Deroanne, C., Lambert, C. A., Lapiere, C. M., Kiss, R., Nusgens, B., & Decaestecker, C. (2006) Neuropathol. Appl. Neurobiol. 32, 575-584.
21. Wu, Z., Martinez-Fong, D., Tredaniel, J., & Forgez, P. (2012) Front Endocrinol. (Lausanne) 3, 184.
22. Ehlers, R. A., Zhang, Y., Hellmich, M. R., & Evers, B. M. (2000) Biochem. Biophys. Res. Commun. 269, 704-708.
23. Gully, D., Labeeuw, B., Boigegrain, R., Oury-Donat, F., Bachy, A., Poncelet, M., Steinberg, R., Suaud-Chagny, M. F., Santucci, V., Vita, N. et al. (1997) J. Pharmacol. Exp. Ther. 280, 802-812.
24. Hassan, S. & Carraway, R. E. (2006) Regul. Pept. 133, 105-114.
25. Hassan, S., Dobner, P. R., & Carraway, R. E. (2004) Regul. Pept. 120, 155-166.
26. Kisfalvi, K., Guha, S., & Rozengurt, E. (2005) J. Cell Physiol 202, 880-890.
27. Servotte, S., Camby, I., Debeir, O., Deroanne, C., Lambert, C. A., Lapiere, C. M., Kiss, R., Nusgens, B., & Decaestecker, C. (2006) Neuropathol. Appl. Neurobiol. 32, 575-584.
28. Zhao, D., Kuhnt-Moore, S., Zeng, H., Wu, J. S., Moyer, M. P., & Pothoulakis, C. (2003) Am. J. Physiol Cell Physiol 284, C1397-C1404.
29. Leyton, J., Garcia-Marin, L., Jensen, R. T., & Moody, T. W. (2002) Eur. J. Pharmacol. 442, 179-186.
30. Lee, L. F., Guan, J., Qiu, Y., & Kung, H. J. (2001) Mol. Cell Biol. 21, 8385-8397.

The invention claimed is:

1. A neutralising antibody which binds to human neurotensin, and has a heavy chain variable region which comprises SEQ ID NO:2 in a H-CDR1 region, SEQ ID NO:3 in a H-CDR2 region and SEQ ID NO:4 in a H-CDR3 region; and a light chain variable region comprising SEQ ID NO:6 in a L-CDR1 region, SEQ ID NO:7 in a L-CDR2 region and SEQ ID NO:8 in a L-CDR3 region.

2. The neutralising antibody of claim 1 wherein the heavy chain variable region has at least 70% identity with SEQ ID NO:1 and/or the light chain variable region has at least 70% identity with SEQ ID NO:5.

3. The neutralising antibody of claim 1 wherein the heavy chain variable region has an amino acid sequence set forth as SEQ ID NO:1 and/or the light chain variable region has an amino acid sequence set forth as SEQ ID NO:5.

4. The neutralising antibody of claim 1 which is a chimeric antibody.

5. The neutralising antibody of claim 1 which is a humanized antibody.

6. The neutralising antibody of claim 1 which is selected from the group consisting of Fv, Fab, F(ab')2, Fab', dsFv, scFv, sc(Fv)2 and diabodies.

7. A nucleic acid sequence which encodes a heavy chain and/or a light chain of an antibody which binds to human neurotensin, and has a heavy chain variable region which comprises SEQ ID NO:2 in a H-CDR1 region, SEQ ID NO:3 in a H-CDR2 region and SEQ ID NO:4 in a H-CDR3 region; and a light chain variable region comprising SEQ ID NO:6 in a L-CDR1 region, SEQ ID NO:7 in a L-CDR2 region and SEQ ID NO:8 in a L-CDR3 region.

8. A vector which comprises a nucleic acid sequence which encodes a heavy chain and a light chain of an antibody which binds to human neurotensin, and has a heavy chain variable region which comprises SEQ ID NO:2 in a H-CDR1 region, SEQ ID NO:3 in a H-CDR2 region and SEQ ID NO:4 in a H-CDR3 region; and a light chain variable region comprising SEQ ID NO:6 in a L-CDR1 region, SEQ ID NO:7 in a L-CDR2 region and SEQ ID NO:8 in a L-CDR3 region.

9. A host cell which has been transfected, infected or transformed by
  a nucleic acid sequence which encodes a heavy chain and/or a light chain of an antibody which binds to human neurotensin, and has a heavy chain variable region which comprises SEQ ID NO:2 in a H-CDR1 region, SEQ ID NO:3 in a H-CDR2 region and SEQ ID NO:4 in a H-CDR3 region; and a light chain variable region comprising SEQ ID NO:6 in a L-CDR1 region, SEQ ID NO:7 in a L-CDR2 region and SEQ ID NO:8 in a L-CDR3 region; or
  a vector comprising the nucleic acid.

10. A pharmaceutical composition which comprises an antibody which binds to human neurotensin, and has a heavy chain variable region which comprises SEQ ID NO:2 in a H-CDR1 region, SEQ ID NO:3 in a H-CDR2 region and SEQ ID NO:4 in a H-CDR3 region; and a light chain variable region comprising SEQ ID NO:6 in a L-CDR1 region, SEQ ID NO:7 in a L-CDR2 region and SEQ ID NO:8 in a L-CDR3 region.

\* \* \* \* \*